United States Patent [19]

Duffett

[11] Patent Number: Plant 5,400

[45] Date of Patent: Feb. 5, 1985

[54] CHRYSANTHEMUM PLANT NAMED CAVALCADE

[75] Inventor: William E. Duffett, Salinas, Calif.

[73] Assignee: Yoder Brothers, Inc., Barberton, Ohio

[21] Appl. No.: 419,006

[22] Filed: Sep. 16, 1982

[51] Int. Cl.[3] ..... A01H 5/00
[52] U.S. Cl. ..... Plt./78
[58] Field of Search ..... Plt./78

*Primary Examiner*—Robert E. Bagwill

*Attorney, Agent, or Firm*—Schwartz, Jeffery, Schwaab, Mack, Blumenthal & Koch

[57] ABSTRACT

A chrysanthemum plant named Cavalcade characterized by the combined characteristics of incurved capitulum form; standard capitulum type; yellow ray floret color; diameter across face of capitulum ranging from 130 to 150 mm. at maturity; uniform nine (9) week photoperiodic flowering response to short days; 55 to 70 cm. plant height when grown single stem with no long days and a low temperature tolerance of 13° C. (55° F.) for initiation and development under controlled short days with a continuous dark period of 12 to 14 hours.

3 Drawing Figures

The present invention comprises a new and distinct cultivar of *Chrysanthemum morifolium,* Ramat., hereinafter referred to by the cultivar name Cavalcade.

Cavalcade is an induced mutation of a light bronze standard seedling named Marmalade, disclosed in applicant's pending application Ser. No. 420,818 filed Sept. 21, 1982 now U.S. Pat. No. PP05281. The planned mutation induction program had the objective of deleting bronze anthocyanins and creating clear yellow ray floret color while retaining all other traits of the parent cultivar.

Cavalcade was discovered and selected as one flowering plant within a population of plants propagated from stock plants of the parent cultivar which had been irradiated as cuttings with an X-ray source of 900 rads by William E. Duffett on July 27, 1979 in a controlled environment in Salinas, Calif.

The first act of asexual reproduction of Cavalcade was accomplished when vegetative cuttings were taken from the initial selection in October, 1979 in a controlled environment in Salinas, Calif. by a technician working under formulations established and supervised by William E. Duffett.

Horticultural examination of selected units initiated April, 1981 has demonstrated that the combination of characteristics as herein disclosed for Cavalcade are firmly fixed and are retained through successive generations of asexual reproduction.

Cavalcade has not been observed under all possible environmental conditions. The phenotype may vary significantly with variations in environment such as temperature, light intensity, and day length. The following observations, measurements and comparisons describe plants grown in Salinas, Calif. under greenhouse conditions which approximate those generally used in commercial practice.

The following traits have been repeatedly observed and are determined to be basic characteristics of Cavalcade which in combination distinguish this chrysanthemum as a new and distinct cultivar:

(1) Incurved capitulum form;

(2) Standard capitulum type;

(3) Yellow ray floret color with minimum color oxidation;

(4) Diameter across face of capitulum ranging from 130 to 150 mm. at maturity;

(5) Uniform nine (9) week photoperiodic flowering response to short days;

(6) Medium plant height (requiring 1 to 2 long day weeks prior to short days to attain a flowered plant height of 80 to 90 cm. for May through October flowerings); and (7) Low temperature tolerance of 13° C, (55° F.) for initiation and development when grown in single stem cut standard programs with a continuous dark period of 12 to 14 hours.

The accompanying photographic drawings show typical inflorescence and foliage characteristics of Cavalcade, with the colors being as nearly true as possible with illustrations of this type. Sheet 1 is a color photograph of Cavalcade grown as a single stem cut standard. Sheet 2 is a black and white photograph showing the top and bottom of leaves of Cavalcade at three stages of growth. Sheet 3 is a black and white photograph of three views of the inflorescence of Cavalcade.

Of the many commercial cultivars known to the present inventor, the most similar in comparison to Cavalcade is #2 Yellow Albatross, an unpatented cultivar. Reference is made to attached Chart A which compares certain characteristics of Cavalcade to those same characteristics of #2 Yellow Albatross.

In comparison to #2 Yellow Albatross, Cavalcade has darker ray floret color, with superior color retention and a slower rate of oxidation; it has a larger diameter across the face of the capitulum by 14 to 25 mm., and taller plant height by approximately 15 cm.; it has similar capitulum form, type and response to short days.

In the following description, color references are made to The Royal Horticultural Society Colour Chart. The color values were determined between 10:30 and 11:00 A.M. on June 30, 1982 under 150 foot-candle light intensity at Salinas, Calif.

CLASSIFICATION

Botanical: *Chrysanthemum morifolium,* Ramat., cv Cavalcade.

Commercial: Cut Yellow Standard.

INFLORESCENCE

Capitulum:

*Form.*—Incurved.

*Type.*—Standard.

*Diameter across face.*—130 To 150 mm.

Corolla of ray florets:

*Color (general tonality from a distance of three meters).*—Yellow.

*Color (abaxial).*—3B to 4A.

*Color (adaxial).*—4B to 4C.

Corolla of disc florets:

*Color(mature).*—6D.

*Color (immature).*—154B.

Reproductive organs:

*Androecium.*—Present disc florets only; scant pollen.

*Gynoecium.*—Present both ray and disc florets.

PLANT

General appearance:

*Height.*—Medium 55 to 70 cm., as a flowering plant from a rooted cutting, with no long days for May through October flowerings and maintaining a minimum nightly 13 hour continuous dark period.

Foliage:

*Color (abaxial).*—147A.

*Color (adaxial).*—147B.

*Shape.*—Deeply lobed and coarsely serrated.

CHART A

COMPARISON OF CAVALCADE AND #2 YELLOW ALBATROSS

| CULTIVAR | RAY FLORET COLOR | CAPITULUM FORM AND TYPE |
|---|---|---|
| CAVALCADE | YELLOW | INCURVED STANDARD |
| #2 YELLOW ALBATROSS | LIGHT YELLOW | INCURVED STANDARD |

| CULTIVAR | DIAMETER ACROSS FACE OF CAPITULUM | PLANT HEIGHT | FLOWER RESPONSE PERIOD |
|---|---|---|---|
| CAVALCADE | 130 to 150 mm. | MEDIUM 55 to 70 cm. | 9 weeks |
| #2 YELLOW ALBATROSS | 115 to 125 mm. | SHORT 45 to 55 cm. | 9 weeks |

COMPARISONS MADE OF PLANTS GROWN AS SINGLE STEM CUT STANDARDS WITH NO LONG DAYS IN SALINAS, CALIFORNIA

I claim:

1. A new and distinct plant of *Chrysanthemum morifolium,* Ramat., known by the cultivar name of Cavalcade, as described and illustrated, and particularly characterized as to uniqueness by the combined characteristics of incurved capitulum form; standard capitulum type; yellow ray floret color; diameter across face of capitulum ranging from 130 to 150 mm. at maturity; uniform nine (9) week flowering response; medium (55 to 70 cm.) plant height when grown single stem; with no long days and a low temperature tolerance of 13° C. (55° F.) for initiation and development under controlled short days with a continuous dark period of 12 to 14 hours.

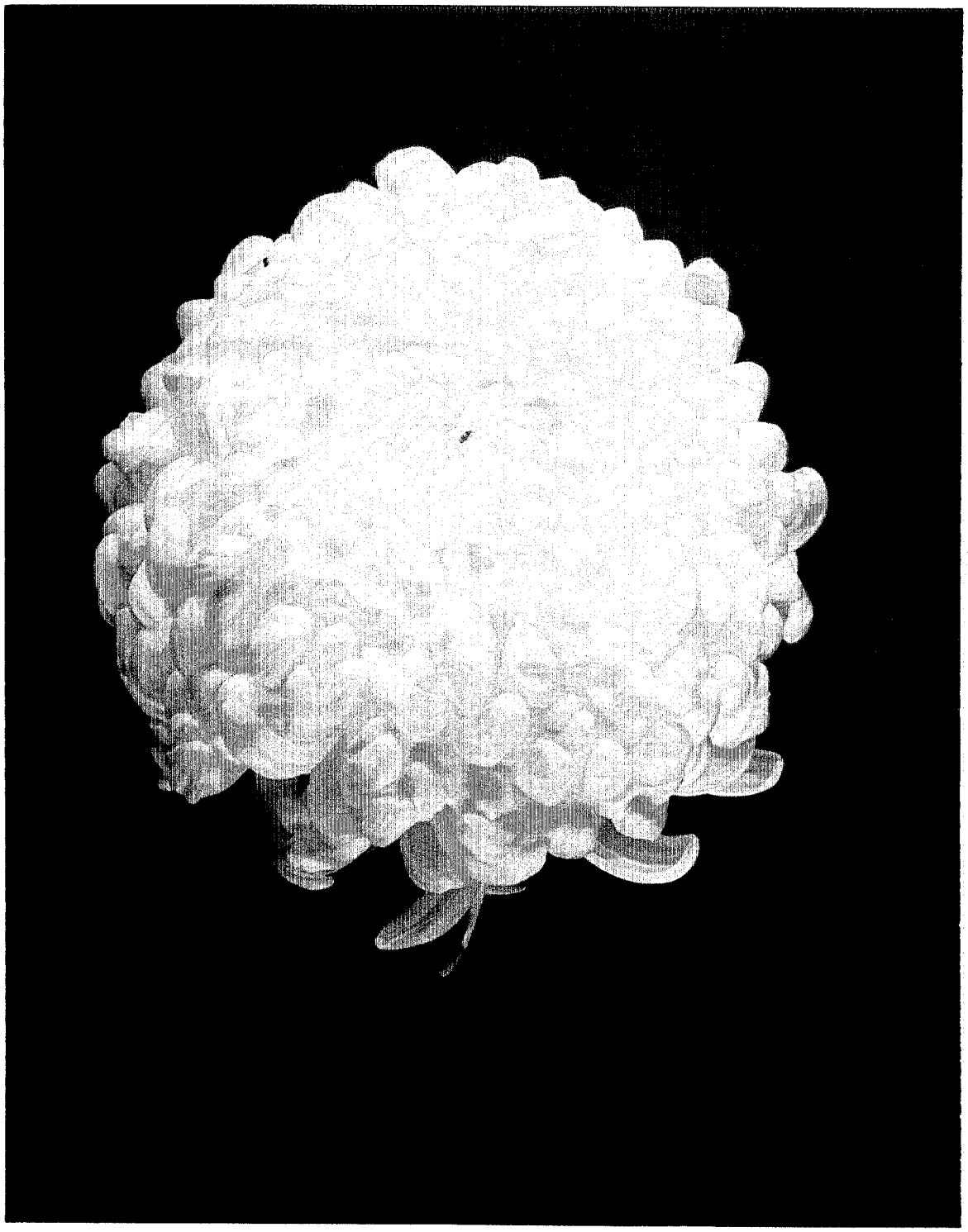

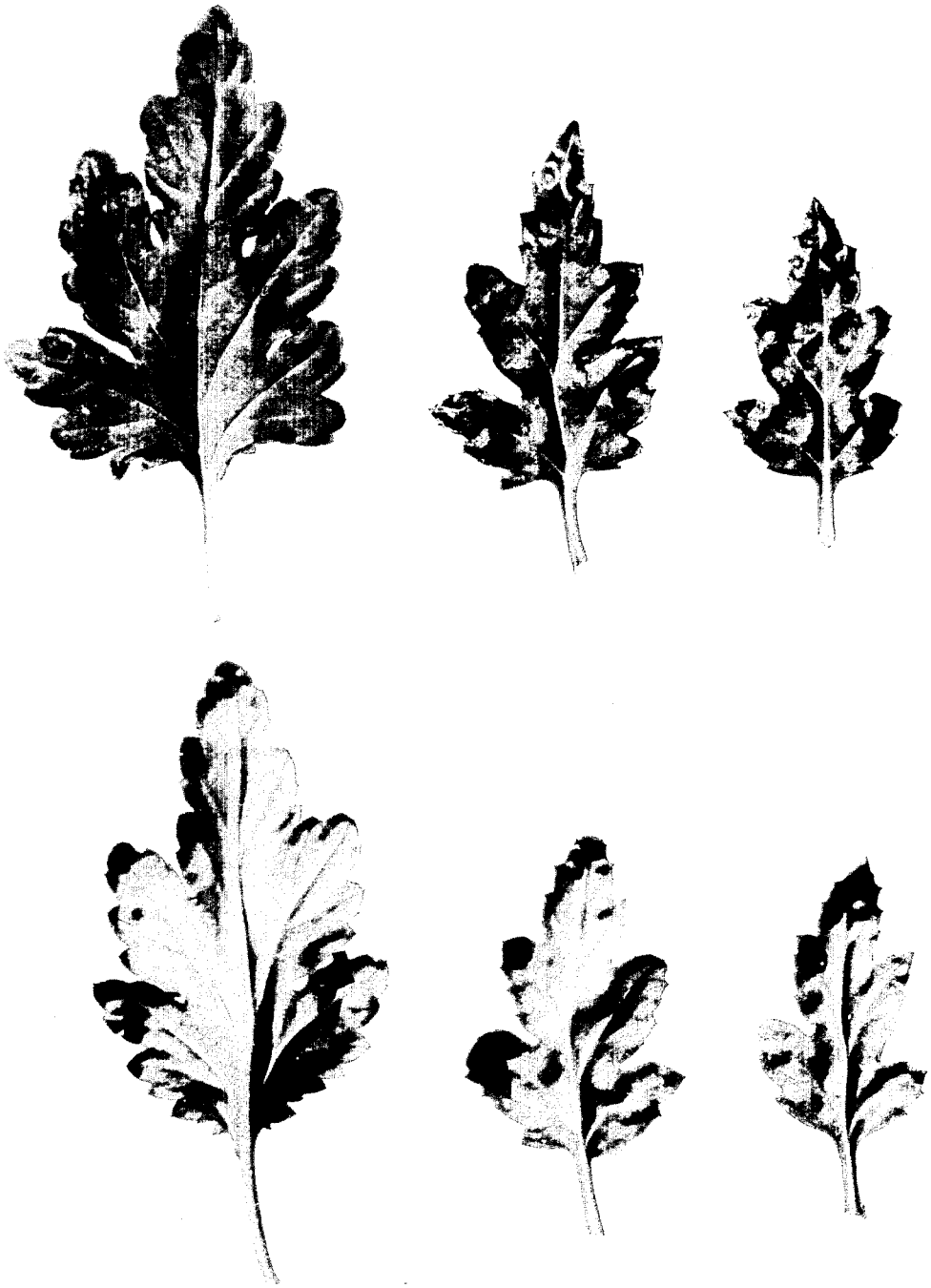

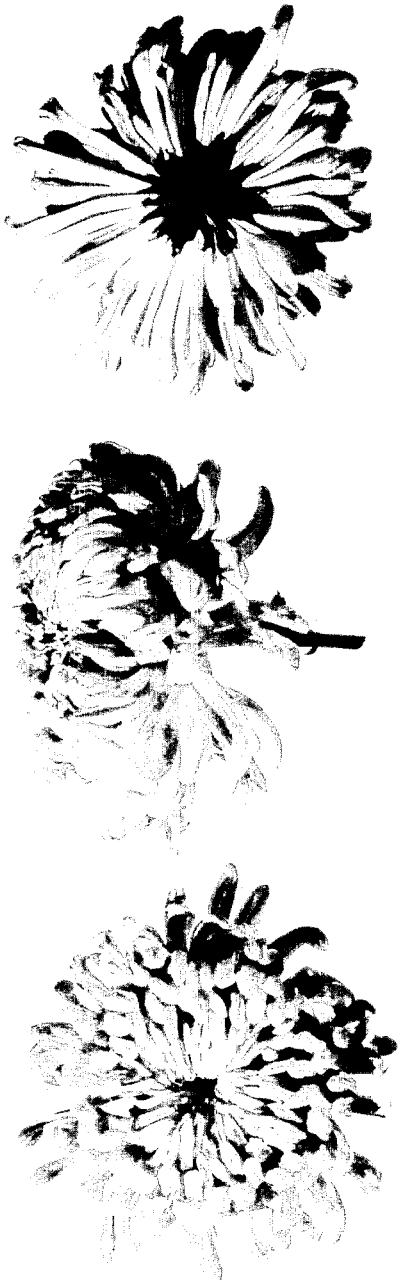

* * * * *